United States Patent [19]
Williams et al.

US005882611A
[11] Patent Number: 5,882,611
[45] Date of Patent: Mar. 16, 1999

[54] CASSETTE AND DELIVERY SYSTEM

[75] Inventors: Hal Williams, San Clemente; Robert Spencer; Alfredo M. Choperena, both of San Juan Capistrano; Jed Kendall, San Clemente, all of Calif.

[73] Assignee: Ethicon, Inc., Somerville, N.J.

[21] Appl. No.: 867,562

[22] Filed: Jun. 2, 1997

[51] Int. Cl.⁶ ...................................................... A61L 2/00
[52] U.S. Cl. ........................... 422/292; 422/28; 206/569; 414/411; 414/416
[58] Field of Search ...................... 422/28, 292; 206/569; 414/411, 416

[56] References Cited

U.S. PATENT DOCUMENTS

| | | | |
|---|---|---|---|
| D. 306,065 | 2/1990 | Williams et al. | D24/9 |
| D. 306,066 | 2/1990 | Williams et al. | D24/9 |
| D. 307,794 | 5/1990 | Williams et al. | D24/51 |
| 4,643,876 | 2/1987 | Jacobs et al. | 422/23 |
| 4,817,800 | 4/1989 | Williams et al. | 206/484 |
| 4,869,286 | 9/1989 | Williams et al. | 137/318 |
| 4,899,519 | 2/1990 | Williams et al. | 53/449 |
| 4,913,196 | 4/1990 | Williams et al. | 141/1 |
| 4,938,262 | 7/1990 | Williams et al. | 141/114 |
| 4,941,518 | 7/1990 | Williams et al. | 141/1 |
| 5,391,360 | 2/1995 | Kochte et al. | 422/292 |

OTHER PUBLICATIONS

"Sterrad 100 Cassette Instructions," Advanced Sterilization Products, 1996.
"Sterrad 100 Cassette Assembly Drawing", Advanced Sterilization Products, 1996.

*Primary Examiner*—Krisanne Thornton
*Assistant Examiner*—Fariborz Moazzam
*Attorney, Agent, or Firm*—Andrew C. Farmer

[57] ABSTRACT

A method for delivering liquids is disclosed wherein a quantity of the liquid is provided within a cell within a cassette. The cassette is received within a sleeve having an open end. A flap at the open end of the sleeve extends inwardly through the open end between the sleeve and cassette to abut a lip on the cassette and hold the cassette therein. Impingement of the flap pushes the flap away from the lip to allow the cassette to move out of the sleeve. A label mounted within the sleeve rotates between a viewable position where it is visible through a window in the sleeve and a retracted position away from the window. Extraction and reinsertion of the cassette into the sleeve moves the label from the viewable to the non-viewable position.

36 Claims, 14 Drawing Sheets

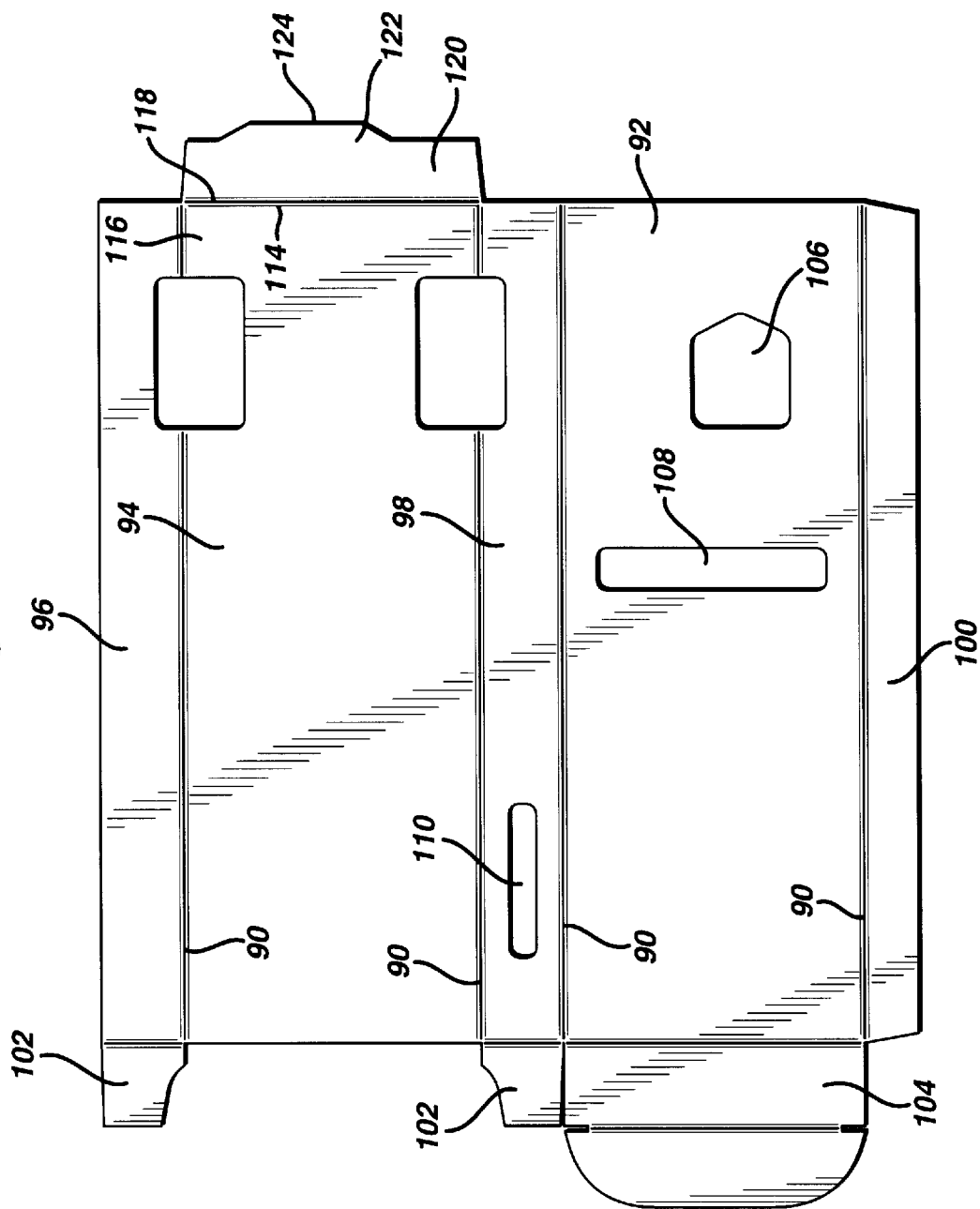

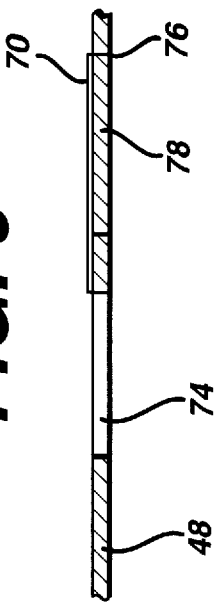
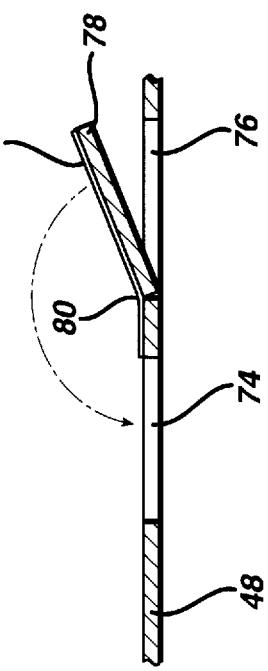
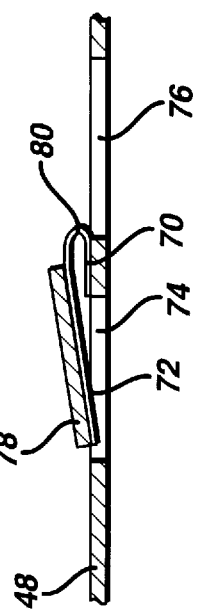
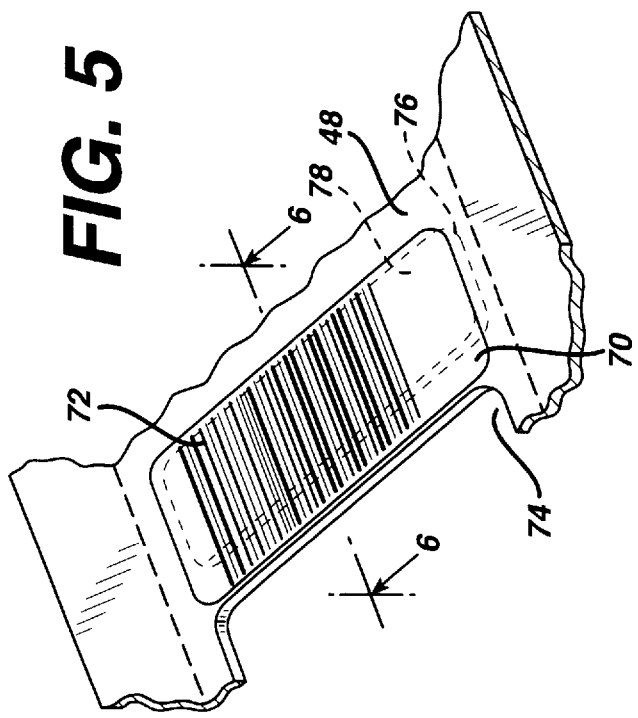

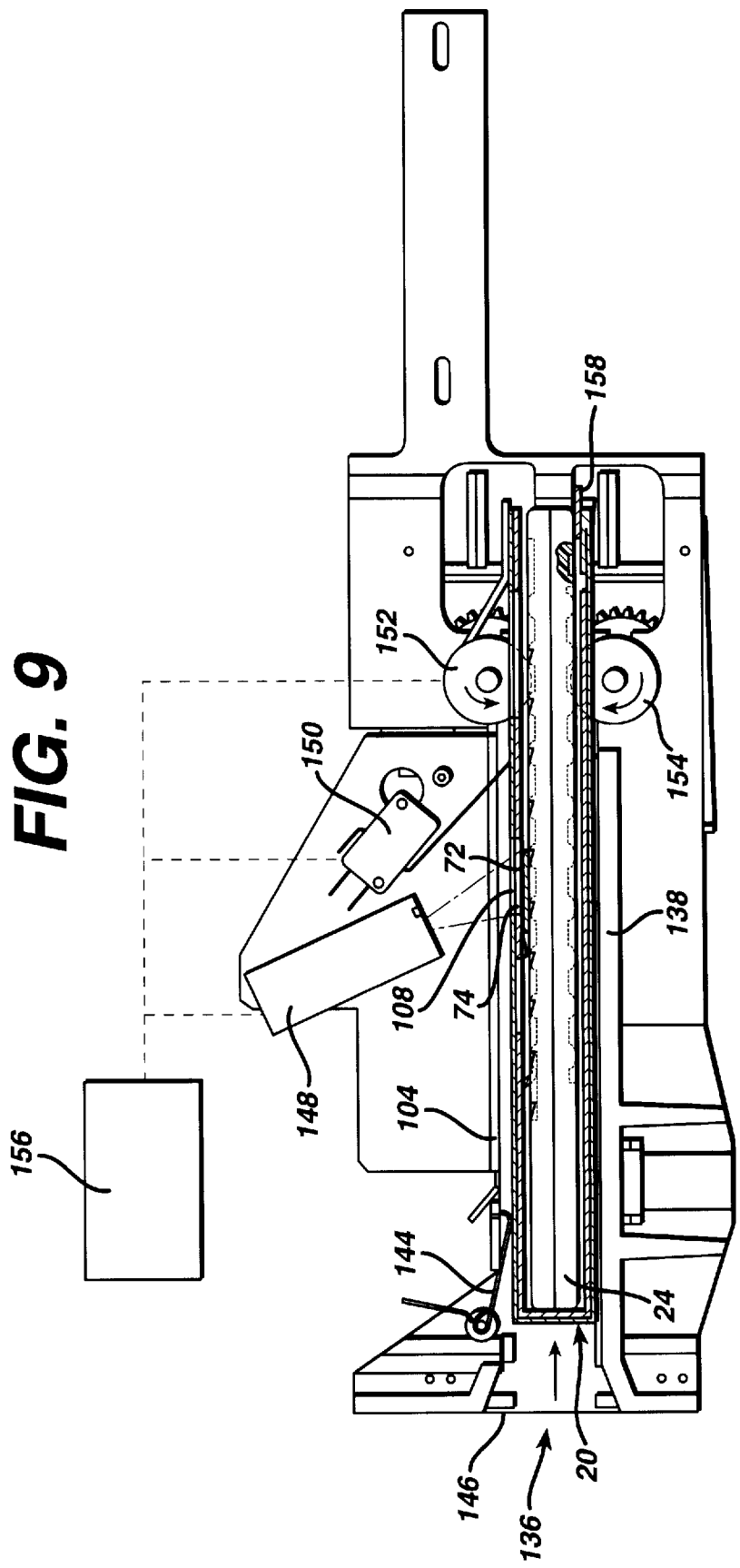

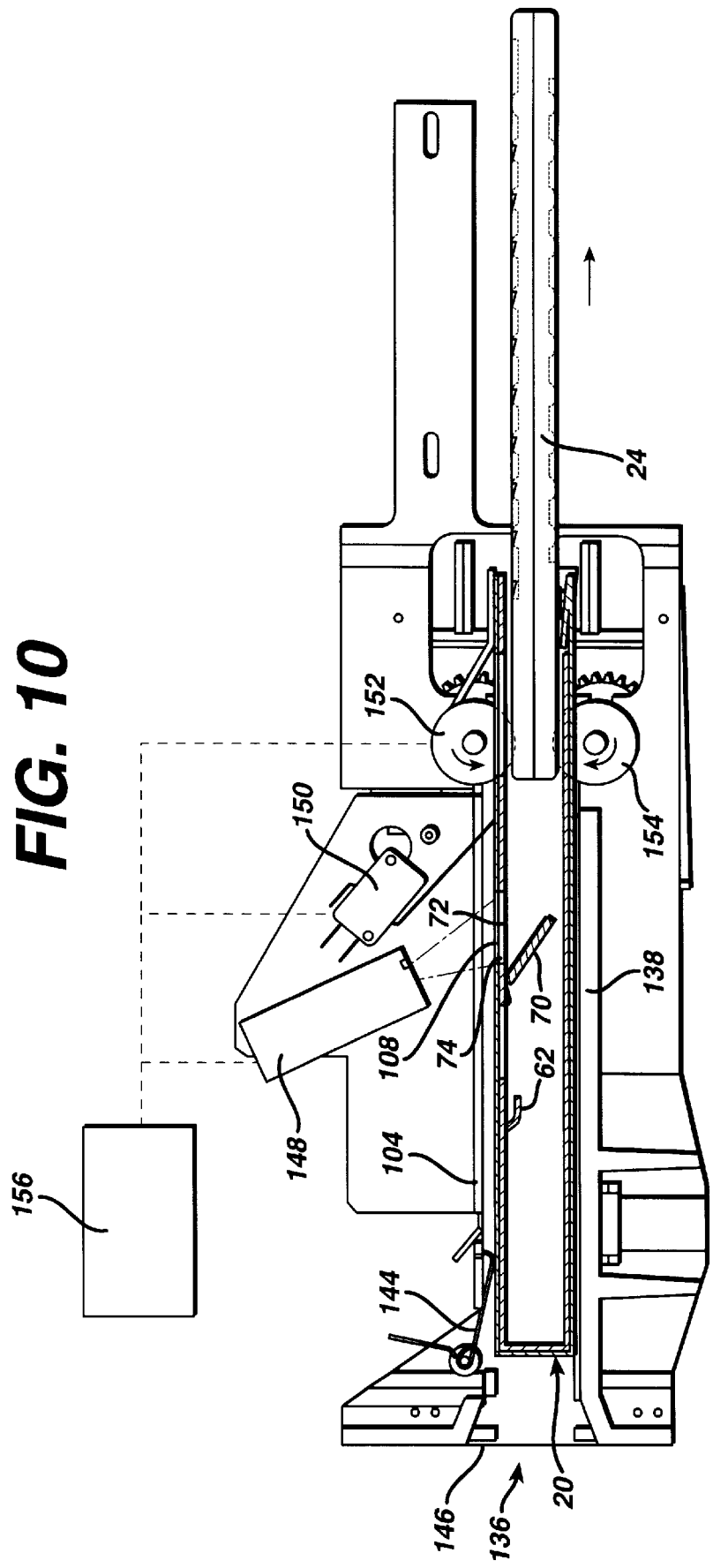

CASSETTE AND DELIVERY SYSTEM

FIELD OF THE INVENTION

The present invention relates to a system for storing and delivering cassettes to a device, and in an important embodiment to the storage and delivery of cassettes containing liquid sterilant to a sterilizing device.

BACKGROUND OF THE INVENTION

U.S. Pat. No. 4,643,876, incorporated herein by reference, discloses a sterilization system in which an agent such a hydrogen peroxide is introduced into a evacuated sterilizing chamber where it is vaporized and allowed to disperse onto the items to be sterilized. After a desired period of time, electrical energy is applied to the chamber to ionize the gas and form a plasma field at a power level sufficient to achieve sterilization.

This system has been successfully commercialized as the STERRAD® Sterilization System and is available from Advanced Sterilization Products, Division of Ethicon, Inc., Irvine, Calif. The system is used in hospitals and other environments where it is operated repeatedly throughout the day by personnel having a widely varying range of understanding of the apparatus. To ensure simple and automatic operation with adequate safeguards with respect to human error, the system employs an automated delivery system for delivering the liquid sterilant to the sterilization chamber. Measured portions of the sterilant, in this case hydrogen peroxide but many other sterilizing agents could be substituted therefor, are provided in rupturable cells within a rigid cassette housing. A transport system maneuvers the cassette within the Sterrad® sterilizer and releases the given quantity of hydrogen peroxide into the sterilization chamber automatically. The cassette and operation of the deliver system are more fully described in the Williams et al. U.S. Pat. Nos. 4,817,800 issued Apr. 4, 1989; 4,913,196 issued Apr. 3, 1990; 4,938,262 issued Jul. 3, 1990; and 4,941,518 issued Jul. 17, 1990, all of which are incorporated herein by reference. In this system, the operator manually grasps the cassette housing and inserts it into the sterilizer. When spent, the cassette is ejected and manually handled by the operator.

This sterilization device with the cassette system offers many advantages. The hydrogen peroxide and plasma kill a wide spectrum of bacteria, viruses, and spores at low temperatures which leave delicate temperature sensitive instruments undamaged. Hydrogen peroxide plasma sterilization meets several environmental and operator safety challenges. After the electromagnetic field producing the plasma is removed, the ionized plasma components recombine to form harmless water and oxygen, avoiding toxic disposal of the sterilant used in the sterilization process. Also, the cassette effectively isolates the operator from the hydrogen peroxide contained therein.

One potential hazard arises from small drops of residual hydrogen peroxide which may be left on the exterior of a spent cassette. A sharp hollow needle pierces the cell which is then pressurized to extract the hydrogen peroxide solution through the needle. In some instances, it is possible for a drop of the solution to escape around the needle and thus remain on the cassette exterior after the extraction process. If an operator's skin or clothing were to contact this droplet, damage could result thereto. Also, operators have been known to accidentally insert a spent cassette into the sterilizer in the mistaken belief that it was actually a new cassette filled with sterilant. Safety mechanisms in the process, such as methods for detecting the presence of sterilant during the sterilization cycle and biological indicators assessing the sterilization cycle efficiency, warn operators of potential cycle failures to prevent inadvertent use of non-sterile instruments thereafter. However, failure of a cycle due to use of a spent cassette entails delays and concomitant expenses.

The present cassette and delivery system encase the cassette within a protective sleeve which isolates the cassette from the operator's hands during all aspects of the cassette handling, thus protecting the operator from contact with any of the sterilant contained therein. Further, an indicator on the sleeve, preferably a moveable label, indicates when the cassette has been used to prevent inadvertent re-use of a spent cassette.

SUMMARY OF THE INVENTION

A cassette assembly for delivering a substance according to the present invention comprises a cassette having at least one cell therein containing a quantity of the substance, the cassette having a first side and a first end. A protective sleeve contains the cassette, and also has a first side and a first end. A retaining member connects to the sleeve by a hinge at the sleeve first end, and is rotatable about the hinge from a first position in which the retaining member blocks the travel of the cassette out of the sleeve through the sleeve first end and a second position in which the retaining member does not block travel of the cassette out of the sleeve through the sleeve first end. Such assembly has particular utility when the substance comprises a hazardous fluid.

Preferably, a biasing means biases the retaining member into the first position. The sleeve can be formed of foldable stock, with the retaining member comprising a flap, the hinge comprising a first fold line in the stock and the biasing means comprising the tendency for the stock to unfold along the first fold line. Preferably, the stock is absorbent, wherein any trace amounts of the substance which may be on the cassette will be absorbed by the stock.

Preferably, the flap extends inwardly of the sleeve from the first fold line to a terminal edge with the terminal edge abutting a first lip on the cassette when the retaining member is in the first position. Preferably, the sleeve first end adjoins the sleeve first side at the first fold line, the cassette first end and the cassette first side are positioned adjacent the sleeve first end and first side respectively, with the lip located on the cassette first side, the flap extending between the cassette first side and the sleeve first side, and the first lip being positioned on the cassette first side. In this aspect of the invention, the second position may comprise the flap being rotated about the hinge toward the first side of the sleeve and away from engagement with the first lip on the cassette.

A retarding means may be provided between the cassette and the sleeve for resisting travel of the cassette out of the sleeve through the sleeve first end. The retarding means may comprise a projection which projects inwardly of the sleeve to engage a detent on the cassette. Preferably, the sleeve is formed of foldable stock and the projection comprises a tab formed of the stock and extending backwards from a fold line to an edge, and wherein it is the edge of the tab that engages the detent. Preferably, the stock is cardboard. The tab preferably moves from a backward extending postion where the tab edge engages the detent on the cassette and a forward facing postion wherein the tab edge is out of engagement with the detent. It may do so in several fashions, including having a length dimension small enough that the tab may rotate forwardly from the backward extending postion to the forward facing postion upon the application of a forward directed force on the cassette relative to the sleeve of a magnitude above a predetermined level, or by being sufficiently flexible so as to buckle upon the application of a forward directed force on the cassette. The magnitude of the predetermined force preferably exceeds one half pound.

The sleeve may be formed of an inner corrugated cardboard layer, with the tab being formed of the inner layer; and an outer cardboard layer, with the flap being formed of the outer layer.

Preferably, the cassette assembly has at least one opening in the sleeve first side whereby a drive wheel may contact the cassette while the cassette is disposed within the sleeve for driving the cassette out of the sleeve through the sleeve first end.

A sterilizing apparatus may comprise a chamber, a source of fluid sterilant contained within at least one cell of a cassette, and a fluid delivery means for delivering the sterilizing fluid from the cell to the chamber An improvement thereto according to the present invention comprises a cassette delivery mechanism for delivering the cassette housing to the fluid delivery system. The cassette delivery system comprises a cassette assembly comprising: the cassette having a first side and a first end; a protective sleeve containing the cassette, the sleeve comprising a first side and a first end; and a retaining member connected to the sleeve by a hinge at the sleeve first end, the retaining member being rotatable about the hinge from a first position in which the retaining member blocks the travel of the cassette out of the sleeve through the sleeve first end; and a second position in which the retaining member does not block travel of the cassette out of the sleeve through the sleeve first end. A receiving port on the sterilizing apparatus receives the cassette assembly and an opening member engages the retaining member when the cassette assembly is received within the receiving port and holds the retaining member in the second position, thereby leaving the cassette free to travel out of the sleeve. Travel means between the receiving port and the fluid delivery mechanism move the cassette out of the sleeve through its first end and into the fluid delivery mechanism.

Preferably, the sleeve abuts a stop at the receiving port, when received within the receiving port, for limiting further travel of the sleeve into the receiving port. A retainer which abuts an edge on the sleeve when the sleeve is received within the receiving port may be provided to inhibit travel of the sleeve out of the receiving port.

A method for delivering a cassette to a device according to the present invention comprises the steps of: (1) placing the cassette within a protective sleeve having a first end; (2) folding a flap on the sleeve inwardly of the sleeve first end to abut a retaining surface on the cassette and block travel of the cassette outwardly of the sleeve through the sleeve first end; (3) inserting an opening member into the cassette first end to abut the flap and move the flap out of engagement with the retaining surface; (4) sliding the cassette out of the sleeve through the sleeve first end and into a the device.

Preferably, a machine, such as a drive wheel operating against the cassette through an aperture in the sleeve, drives the cassette out of the sleeve. One of skill in the art will recognize that many alternative means may be substituted therefor. Such a drive wheel, or alternative device, may be employed to drive the cassette assembly into contact with the opening member. Preferably, an automatic controller controls the operation of this process.

BRIEF DESCRIPTION OF THE DRAWINGS

FIG. 4 is a plan view of an unfolded blank of an outer layer of the sleeve of FIG. 1;

FIG. 5 is a perspective view of an identifying label according to the present invention on the sleeve inner layer of FIG. 3;

FIG. 6 is a sectional view of the label of FIG. 5 shown in the retracted position;

FIG. 7 is a sectional view as in FIG. 6, showing the label in a transitional orientation;

FIG. 8 is a sectional view as in FIG. 6, showing the label in the exposed orientation wherein the label is viewable through an aperture;

FIG. 9 is a cut-away view of the cassette and sleeve of FIG. 1 positioned within a cassette handling mechanism and showing the cassette upon entry into the handling system;

FIG. 10 is a view of the cassette, sleeve and handling system in accordance with FIG. 9 and showing the cassette traveling out of the sleeve;

DETAILED DESCRIPTION OF THE INVENTION

Figure 1:
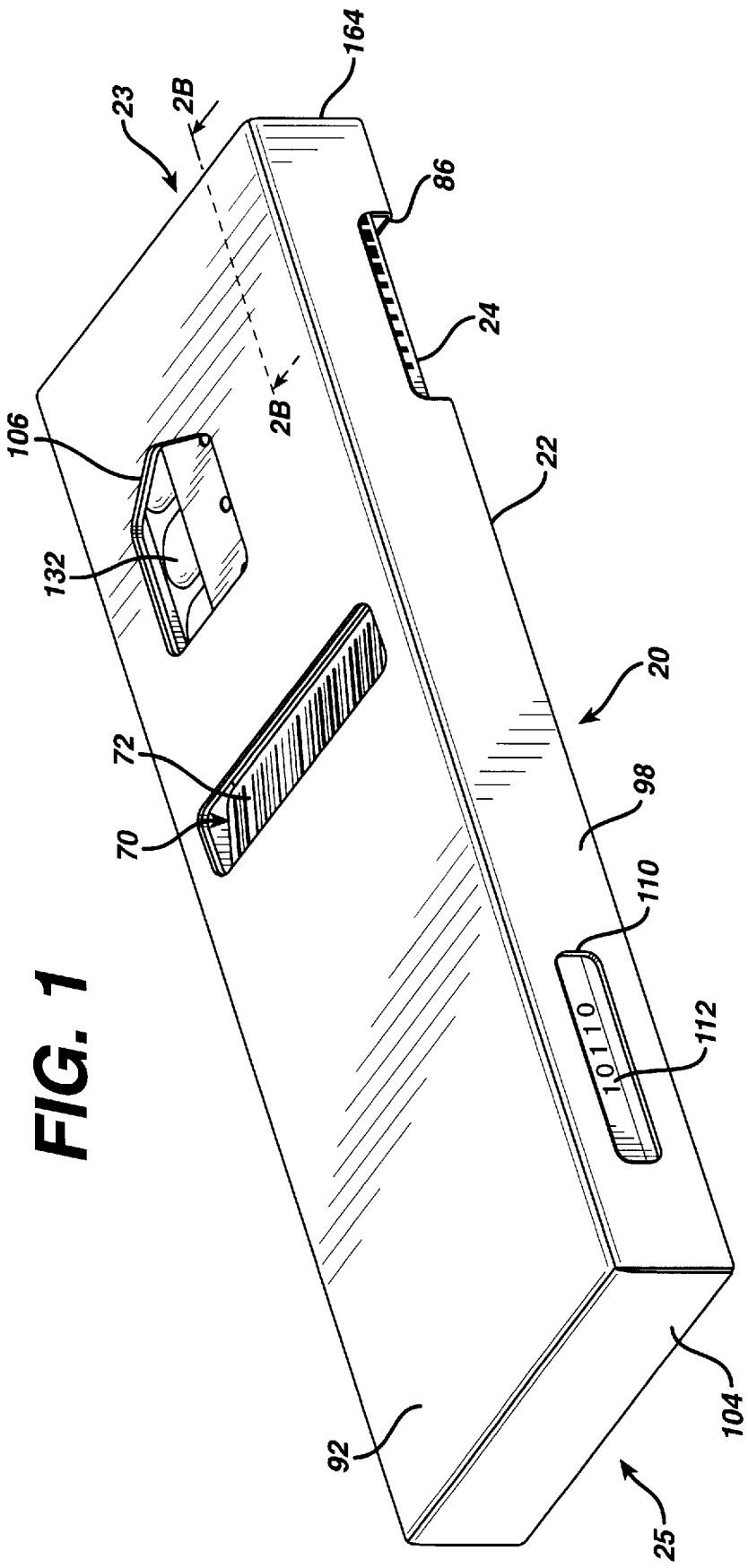
FIG. 1 is a perspective view of a cassette within a sleeve in accordance with the present invention.
Figure 2:
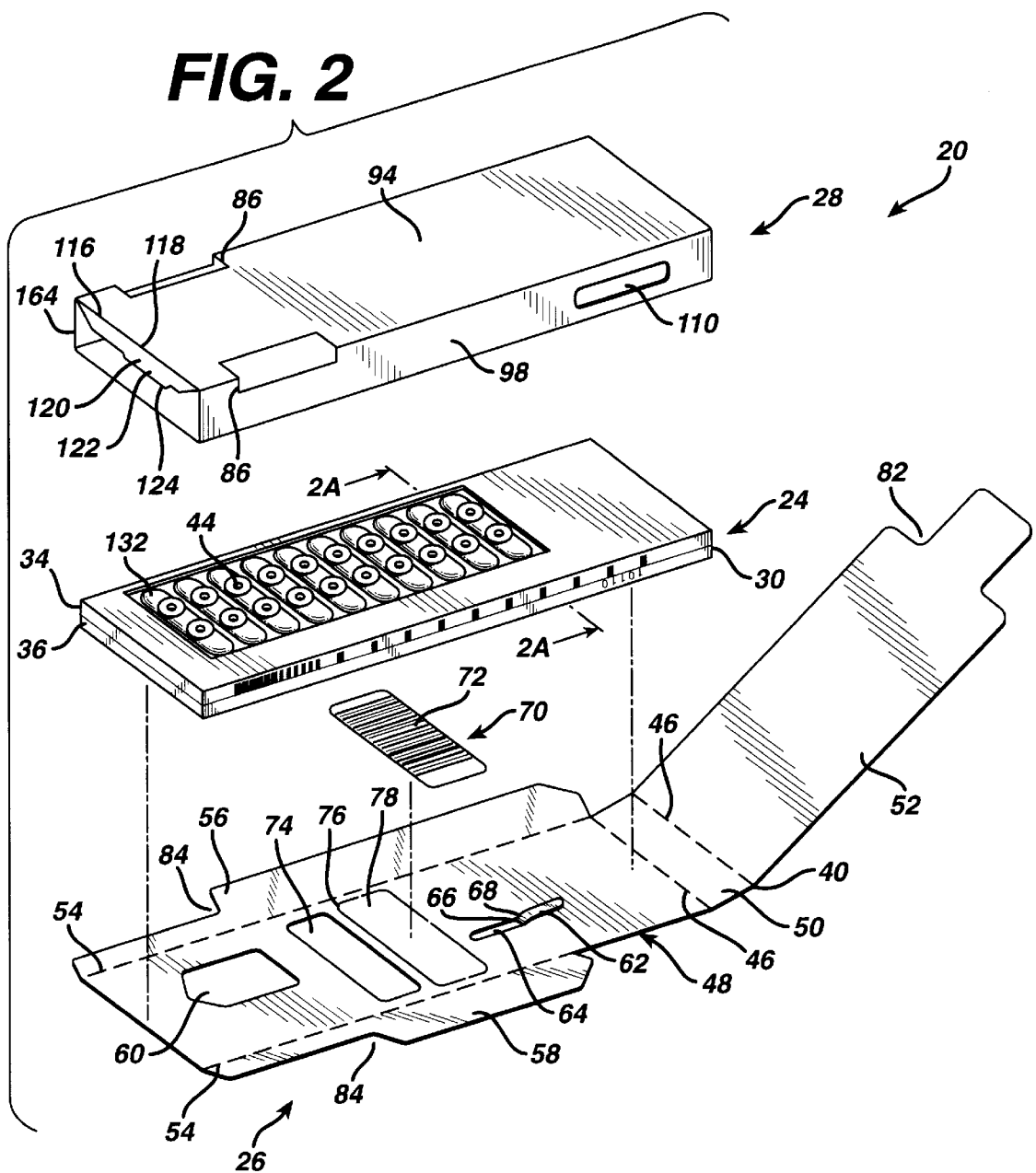
FIG. 2 is an exploded view of the cassette and sleeve of FIG. 1.
Figure 2A:
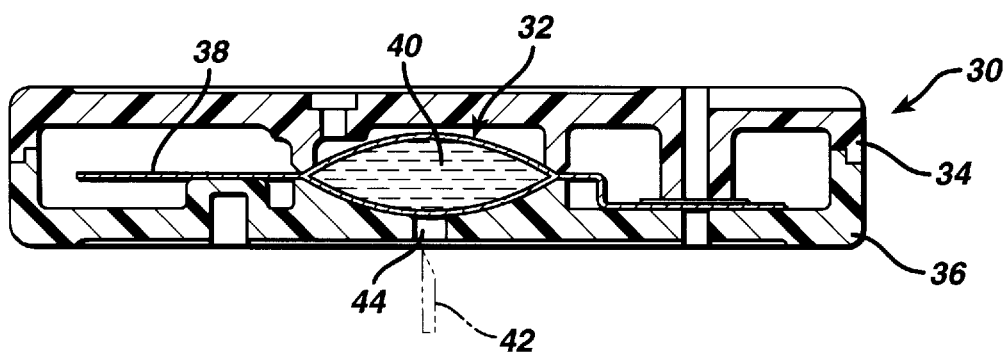
FIG. 2A is a sectional view taken along line 2A—2A of FIG. 2.
Figure 2B:
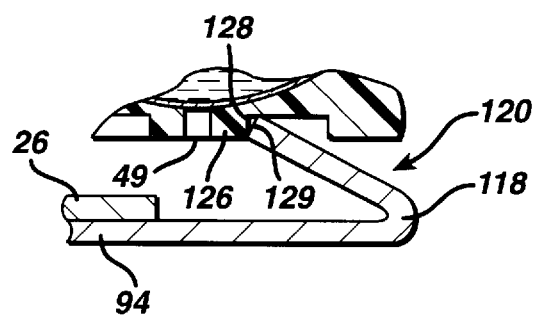
FIG. 2B is a sectional view taken along line 2B—2B of FIG. 1.

FIG. 1 illustrates an assembled cassette assembly 20 comprising a sleeve 22 containing a cassette 24 and the exploded view of FIG. 2 illustrates the components of the cassette assembly 20 in more detail. The sleeve 22 has an open end 23 and a closed end 25 and comprises an inner layer 26 of corrugated cardboard and an outer layer 28 of an attractive pressboard material. The cassette 24 comprises an elongated, rectangular plastic shell 30 containing a plurality of cells 32 containing a 58% solution of hydrogen peroxide. As seen in FIG. 2a, the cassette shell 30 is formed of an upper housing section 34 which mates with a lower housing section 36 to capture and to enclose a cell strip 38. The cell strip 38 is formed of a flexible material and contains the cells 32. Each cell 32 contains a precisely measured amount of hydrogen peroxide 40. Of course, other liquid sterilants may be substituted therefor. Preferably, the cassette shell 30 and cell strip 38 are formed of suitable polymers such as polystyrene and polyethylene, respectively. However, one of skill in the art will recognize that other materials may be substituted therefor. Each of the cells 32 is accessible by a hollow needle 42 through an aperture 44 in the cassette shell 30.

Figure 3:
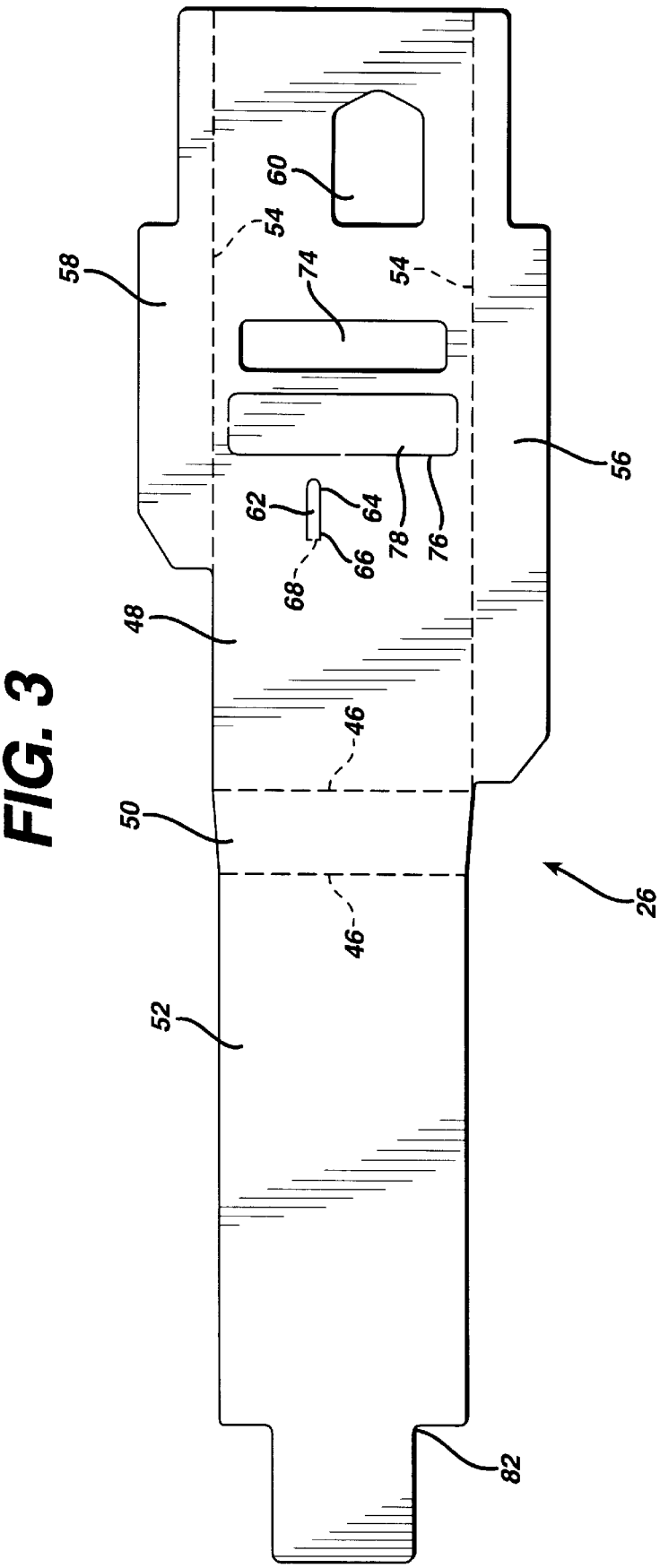
FIG. 3 is a plan view of an unfolded blank forming an inner layer of the sleeve of FIG. 1.

Returning to FIG. 2, the sleeve inner layer 26 wraps about the cassette 24. Thus, if any small droplets of the hydrogen peroxide solution are left on the outside of the cassette 24 after use, they will be absorbed by the cardboard of the sleeve inner layer 26 thereby preventing contact with an operator's hands or clothing. The sleeve inner layer 26 provides several other important functions as will become apparent. As is also seen in FIG. 3, the sleeve inner layer 26 folds about a pair of parallel fold lines 46 to form an upper panel 48, an end panel 50, and a lower panel 52. A pair of longitudinal fold lines 54 forms a first side panel 56 and second side panel 58. A large arrow shaped aperture 60 in the upper panel 48 points toward the sleeve open end 23. Also, a tab 62 comprises a small longitudinally elongate cutout that remains attached at its rearward end 66 (toward the sleeve closed end) thereby forming a fold line 68 about which the tab 62 rotates through 180°.

A label 70, preferably with computer readable indicia 72 such as a bar code, identifies the cassette assembly 20. A large lateral rectangular aperture 74 forms a window through which the label 70 becomes visible. A rectangular cutout 76 sits immediately rearward of the window aperture 74 and forms a removable panel 78 of cardboard, which fits within the cutout 76. The label 70 has adhesive on its surface opposite the indicia 72 and attaches to the removable panel 78 and to the inner sleeve upper panel 48 between the cutout 76 and window aperture 74. As shown in FIGS. 5 to 8, this forms a hinge 80 which allows the label to rotate through 180° from a position as shown in FIG. 6 wherein the removable panel 78 is received within the cutout 76 and the label indicia 72 are not visible through the window aperture 74, through the position shown in FIG. 7, to the position shown in FIG. 8 wherein the label indicia 72 becomes visible through the window aperture 74.

Returning to FIG. 2, cutouts 82 at the lateral side edges of the inner sleeve upper panel 48 near the sleeve open end 23, and additional cutouts 84 aligned therewith in the inner sleeve first and second side panels 56 and 58, provide access to the cassette 24 through the sleeve inner layer 26. Similar cutouts 86 are provided in the sleeve outer layer 28 in registry with the cutouts 82 and 84 to provide access to the cassette 24 through the entire sleeve 22.

FIGS. 2 and 4 best illustrate the structure of the sleeve outer layer 28. It is formed of folded pressboard stock, but of course could be formed of other folded stock material, such as a suitable polymer, or could be molded or formed in some other fashion to form an equivalent structure to that disclosed here. Longitudinal fold lines 90 form a top panel 92, bottom panel 94, a first side panel 96 and a second side panel 98, which correspond to the sleeve inner layer 26, upper panel 48, lower panel 52, first side panel 56 and second side panel 58, respectively. The longitudinal fold lines 90 also form a glue flap 100 which seals to the first side panel 96 to form the three dimensional structure of the outer sleeve layer 28. Side tabs 102 and a foldable flap 104 form the closed end 25 of the sleeve outer layer 28. Of course, other closure means such as glue flaps may be substituted therefor. An arrow shaped aperture 106 and a rectangular window 108 in the top panel 92 register with the corresponding openings 60 and 74 in the sleeve inner layer 26. The rectangular window 110 in the second side panel 98 provides viewing for indicia 112 on the cassette 24.

A lateral fold line 114 at the forward end 116 of the bottom panel 94 forms a hinge 118 about which rotates a retaining flap 120. The retaining flap 120 extends from the fold line 114 to terminate in a tang 122; a terminal edge 124 of which engages the cassette 24 to retain the cassette 24 within the sleeve 22. An annular post 126 surrounds each of the piercing apertures 44 in the cassette 24 such that the aperture 44 extends axially through the post 126. The post has a vertical annular sidewall 128 against which the terminal edge 124 abuts. The retaining flap 120 performs a surprisingly good job of holding the cassette 24 within the sleeve 22. Even fairly vigorous shaking will not dislodge the cassette 24 from the sleeve 22.

A fresh cassette assembly 20 having its cells 32 filled with hydrogen peroxide is configured as follows: the cassette 24 is received within the sleeve inner layer 26. The label 70 is folded into the position shown in FIG. 8 wherein the label indicia 72 are visible through the window apertures 74 and 108. Also, the tab 62 is folded over 180° to face rearwardly. The cells 32 are received within chambers within the cassette shell 30, the outer surface 132 of which is rounded. The tab 62 engages this rounded outer surface 132 to provide a certain degree of resistance to movement between the cassette 24 and the sleeve 22. The sleeve inner layer 26 is received within the sleeve outer layer 28 with the retaining flap 120 folded over the inner layer 26 and into the sleeve 22 where its terminal edge 124 abuts the annular post vertical wall 128 on the cassette 24 thereby retaining the sleeve inner layer 26 and the cassette 24 within the sleeve outer layer 28.

The cassette assembly 20 is intended for use with an automatic cassette extraction mechanism 134 as is shown in FIGS. 9 to 15. Turning to FIG. 9, the extraction mechanism 134 comprises a receiving slot 136 sized to receive the cassette assembly 20 with its sleeve open end 23 forward. The receiving slot 136 is outlined by a lower wall 138, an upper wall and two opposing sidewalls 142 (see also FIG. 15). A spring-loaded door 144 at an entrance 146 to the receiving 136 closes the receiving slot 136 when not in use and provides a downward biasing force against the cassette 24 to hold it firmly against the lower wall 138.

A bar code reader 148 is positioned above the lower wall 138 in such a fashion as to read the label indicia 72 as the cassette 24 is inserted into the receiving slot 136. A pressure switch senses the presence of a cassette 24 within the receiving slot 136. A position sensing switch 150 engages the bar-code reader 148, and also engages an upper drive wheel 152 and a pair of lower drive wheels 154. If the bar code reader 148 fails to read the presence of a valid bar code label 70, then the drive wheels 152 and 154 will reverse to eject the cassette assembly 20 from the receiving slot 136. Assuming that the bar code reader 148 successfully reads the label 70, the label information, including lot code and shelf life data, will be fed to a control unit 156 for use in the sterilization control process. The control unit 156 is also operably connected to the position sensing switch 150 and the drive wheels 152 and 154 to control the label reading and cassette extraction process. Any suitable control unit may be employed, such as a microprocessor based automatic control system, and multiple controllers may be used for controlling various aspects of the operation described herein.

Figure 15:
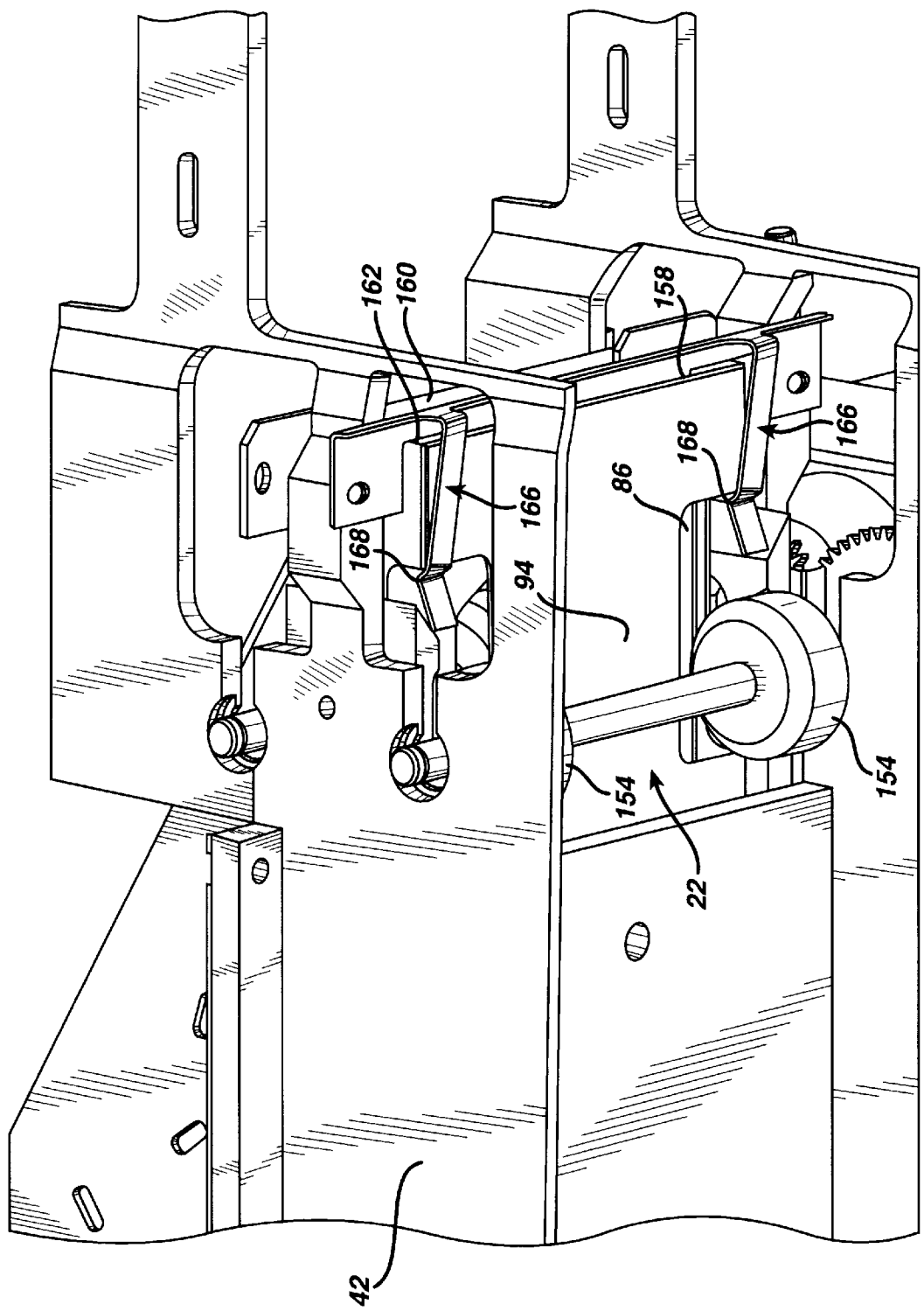
FIG. 15 is a front and bottom cut-away perspective view of the cassette handling system.

As is best seen in FIGS. 9 and 15, as the cassette assembly 20 is received into the receiving slot 136, a projection or opener 158 on the loading mechanism 134 slides between the cassette 24 and retaining flap 120 to rotate the retaining flap downwardly and out of engagement with the cassette 24. This allows the cassette 24 to slide outwardly of the sleeve 22. The opener 158 extends laterally from a bracket 160 and an edge 162 on the bracket 160 adjacent the opener 158 abuts forward edges 164 of the sleeve 22 to limit forward movement of the sleeve 22. A pair of spring clips 166 project laterally and slightly upwardly from the bracket 160. Each of the spring clips 166 has a upwardly extending lip 168 thereon which slides into the cut outs 82 and 86 of the sleeve inner layer 26 and outer layer 28, respectively, to hold the sleeve 22 firmly in position. With the cassette assembly 22 in this position, the lower drive wheels 154 also protrude through the cut outs 82 and 86 to engage the cassette lower housing 36, and the upper drive wheel 152 protrudes through the arrow shaped apertures 60 and 106 to engage the cassette upper housing 34. Thus, rotation of the drive wheels urges the cassette 24 outwardly of the sleeve 22 through its open end 23.

Resistance to movement between the cassette 24 and sleeve 22 provided by the tab 62 ensures that if the cassette assembly 20 is not already properly positioned against the bracket edge 162, the sleeve 22 will move forwardly with the cassette 24 until the sleeve 22 is properly in position. At this point, the resistance provided by the tab 62 can no longer restrain movement of the cassette 24 and it will move forwardly out of the sleeve 22.

Figure 16:
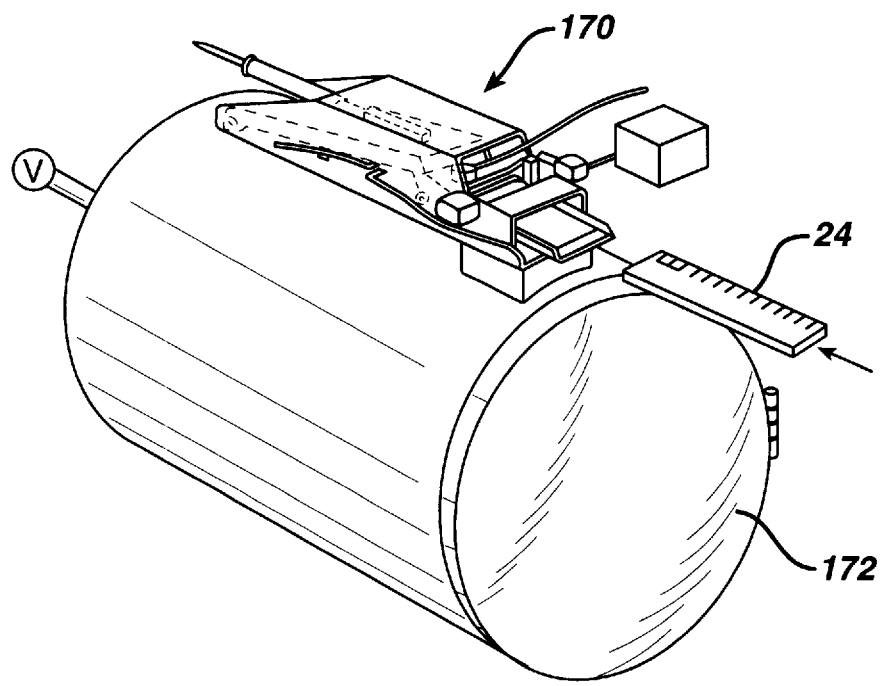
FIG. 16 is a perspective view of a sterilizing chamber and fluid extraction mechanism.

Turning to FIG. 10, as the cassette 24 moves out of the sleeve 22, the springiness of the label 70 and the weight of the removable panel 78 urge the label 70 to hang downwardly about its hinge point 80. The cassette 24 then moves out of the extraction mechanism 134 and into a fluid handling system 170 such as is shown in FIG. 16, with the cassette extraction mechanism 134 removed for clarity. The fluid handling system 170 extracts the measured quantity of hydrogen peroxide from a cell 32 through the needle 42 (see FIG. 2A) to deliver it to a sterilization chamber 172 to sterilize articles (not shown) contained therein. Operation of this mechanism is more fully described in the Williams et al. U.S. Pat. Nos. 4,817,800 issued Apr. 4, 1989; 4,913,196 issued Apr. 3, 1990; 4,938,262 issued Jul. 3, 1990; and 4,941,518 issued Jul. 17, 1990, all of which are incorporated herein by reference.

Figure 11:
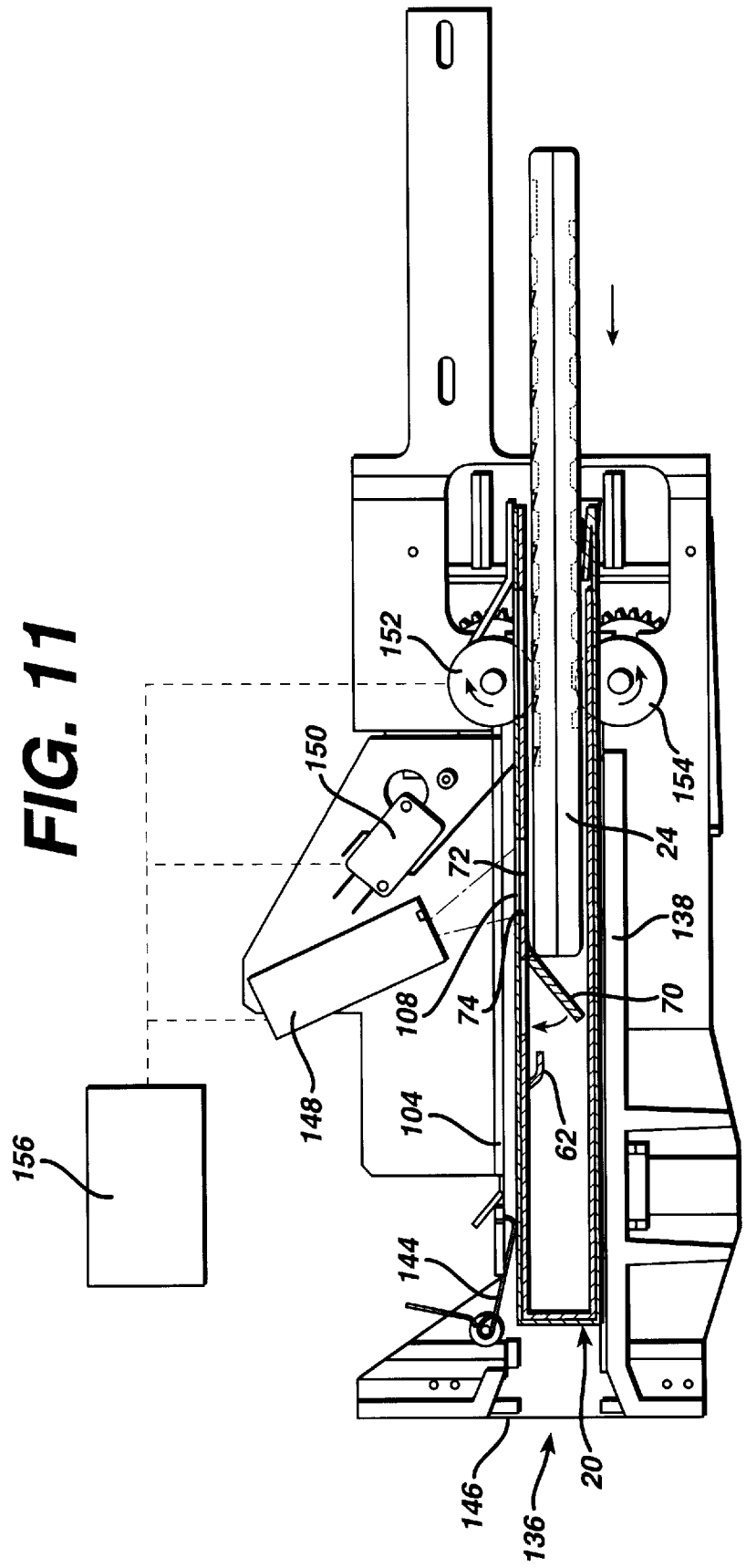
FIG. 11 is a view of the cassette, sleeve and handling system in accordance with FIG. 9 and showing the cassette traveling back into the sleeve.
Figure 12:
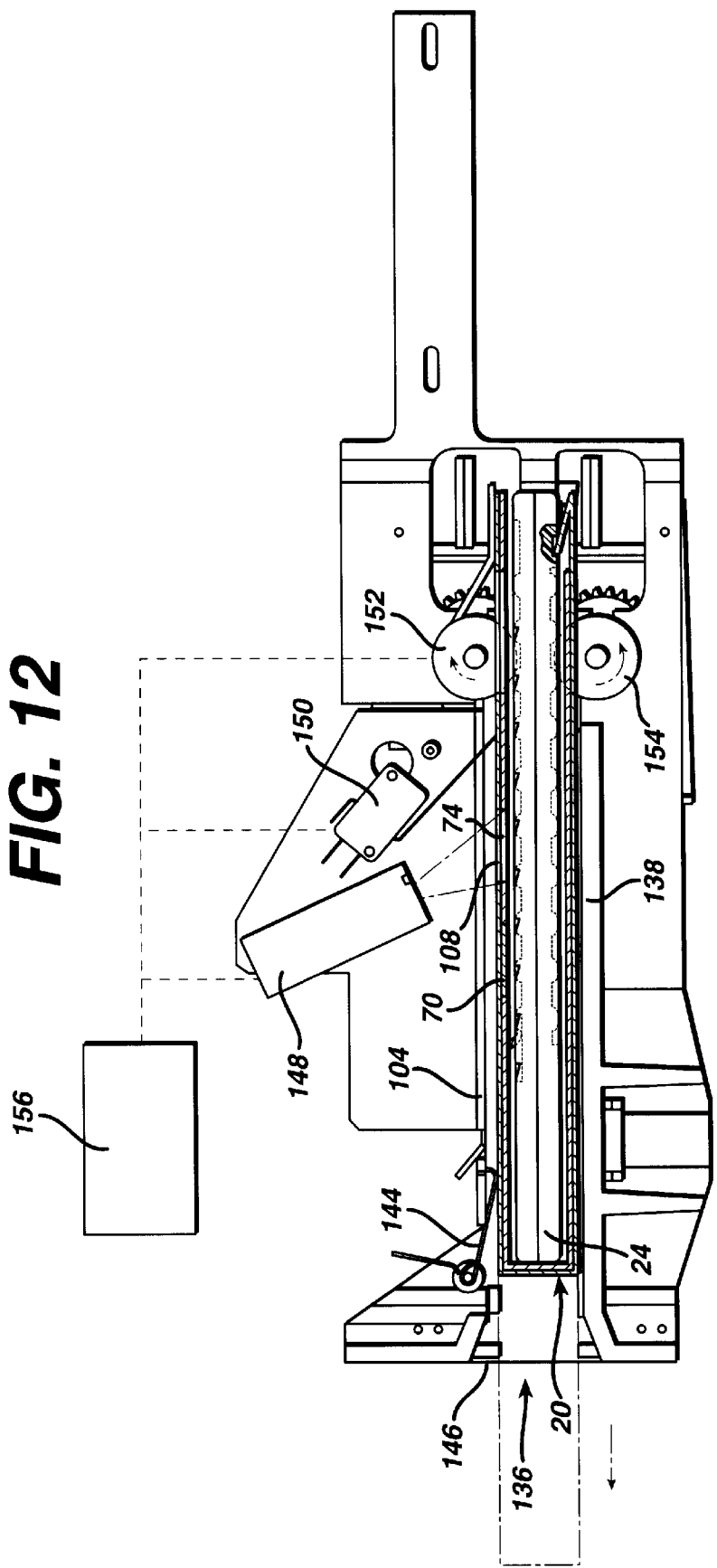
FIG. 12 is a view of the cassette, sleeve and handling system in accordance with FIG. 9 and showing the cassette repositioned within the sleeve in preparation for leaving the handling system.
Figure 13:
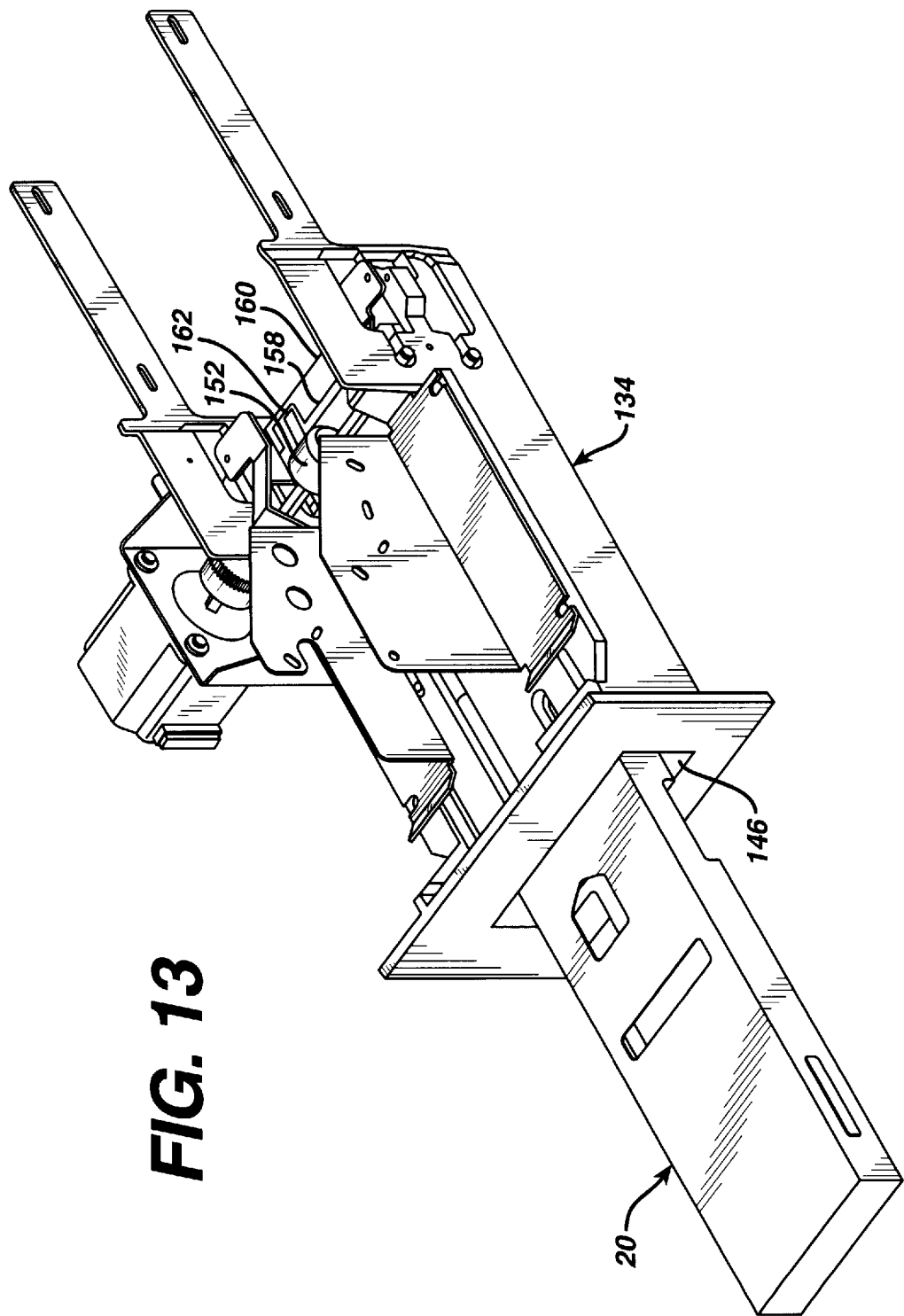
FIG. 13 is a cut-away perspective view of the cassette and sleeve assembly entering the cassette handling assembly.
Figure 14:
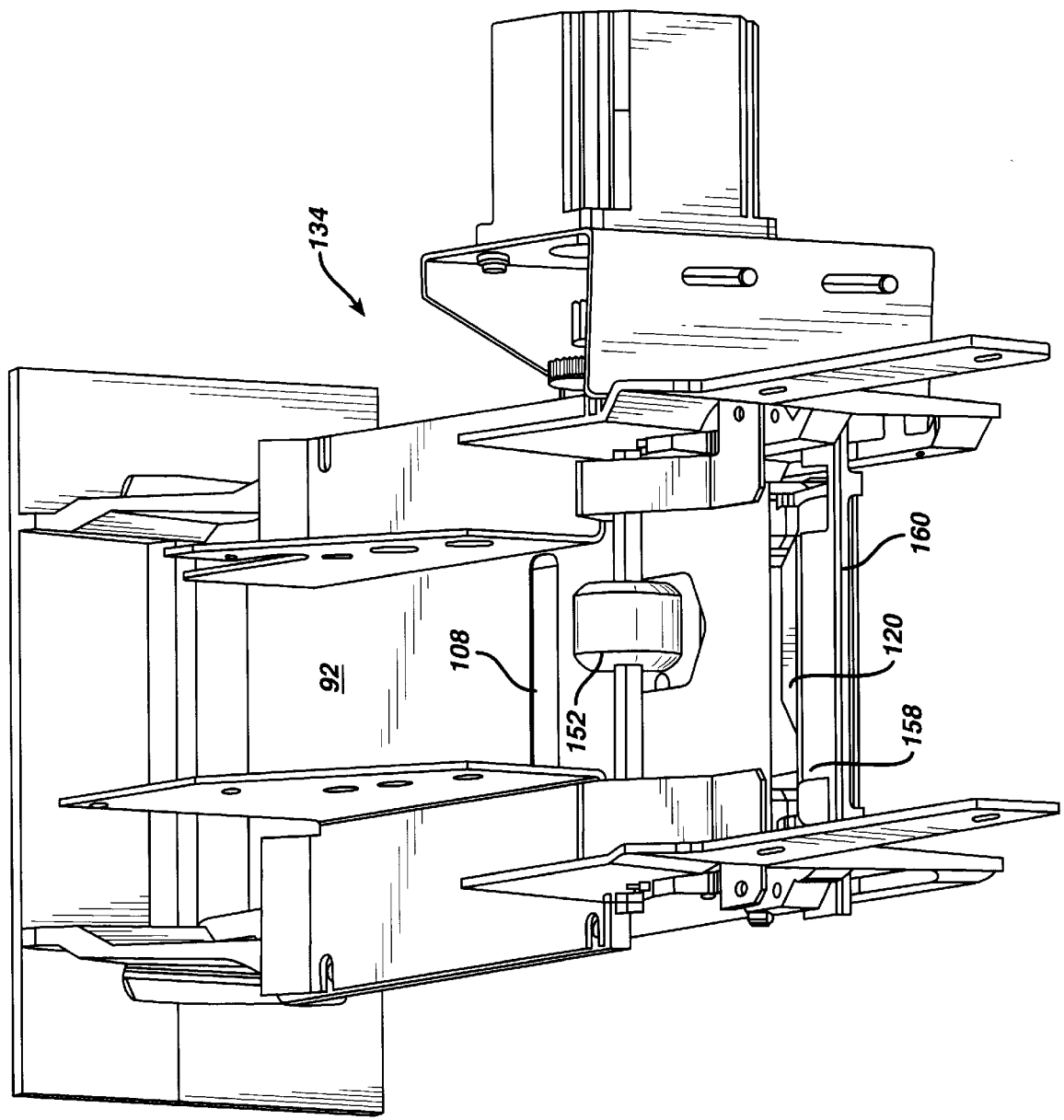
FIG. 14 is a front and top cut-away perspective view of the cassette handling system.

When spent, the cassette 24 returns from the fluid handling system 170 and the drive wheels 152 and 154 push it home into the sleeve 22, as shown in FIG. 11. As the cassette 24 moves into the sleeve 22, its rearward end contacts the label 70 causing it to rotate backwards to the position illustrated in FIG. 6 wherein the label indicia 72 are not visible exterior of the sleeve 22. Turning to FIG. 12, the cassette assembly 20 then moves outwardly of the receiving slot 136. The opener 158 slides out of the sleeve 22 thus allowing the retaining flap 120 to move upwardly into engagement with the cassette 24. The cassette assembly 20 is thus ejected from the receiving slot 136 with the cassette 24 firmly received with the sleeve 22.

Any drops of hydrogen peroxide solution which may remain on the outside of the cassette, although unlikely, would nevertheless be absorbed and retained by the sleeve inner layer 26 thereby protecting an operator therefrom. If the spent cassette is reinserted in to the receiving slot 136, the indicia 72 on the label 70 will not be visible due to the folding over of the label 70 during the cassette reinsertion. When the bar code reader 148 senses the lack of identifying indicia 72, the control unit 156 instructs the drive wheels 152 and 154 to immediately eject the cassette assembly 20. Of course, other actions can result in rejection of the cassette assembly 20. For instance, the control unit could be programmed to reject the cassette assembly if the bar code data indicates that the cassette assembly 20 has exceeded its shelf life, or if the lot code has previously been identified as rejected.

While the invention has been described with regard to a particular embodiment thereof, those skilled in the art will understand, of course, that the invention is not limited thereto since modifications can be made by those skilled in the art, particularly in light of the foregoing teachings. Reasonable variation and modification are possible within the foregoing disclosure of the invention without the departing from the spirit of the invention.

For example, the novel cassette assembly and handling techniques may be applied to other processes outside of sterilization. The techniques described herein have utility for handling a variety of cassettes, such as for example, cassettes containing reagents for chemical or medical tests. The contents of the cassette need not be liquid and the invention is not limited to any specific material or method of extracting such material from the cassette.

Further, other structures than presented herein may accomplish the teachings of the present invention. The retaining flap 120 need not face inwardly of the sleeve 22 to abut a surface on a face of the cassette. Instead, it could abut an end of the cassette, or could abut a surface on the sleeve, such as a folded-in lip on the edge of the sleeve opposite the flap 120 at the cassette open end. In this case, the spring in the material of the sleeve would hold the flap 120 in place.

Other means of providing resistance to movement between the cassette 20 and the sleeve 22 could substitute for the tab 62. For instance, rearwardly facing projections could be formed on the sleeve, or attached thereto.

What is claimed is:

1. A cassette assembly for delivering a substance, the assembly comprising:

a cassette having at least one cell therein containing a quantity of the substance, and the cassette further comprising a first side and a first end;

a protective sleeve containing the cassette, the sleeve comprising a first side and a first end; and a retaining member connected to the sleeve by a hinge at the sleeve first end, the retaining member being rotatable about the hinge from a first position in which the retaining member blocks the travel of the cassette out of the sleeve through the sleeve first end; and a second position in which the retaining member does not block travel of the cassette out of the sleeve through the sleeve first end.

2. A cassette assembly according to claim 1 and further comprising biasing means biasing the retaining member into the first position.

3. A cassette assembly according to claim 2 wherein the sleeve is formed of foldable stock, the retaining member comprises a flap, the hinge comprises a first fold line in the stock and the biasing means comprises the tendency for the stock to unfold along the first fold line.

4. A cassette assembly according to claim 3 wherein the stock is absorbent, wherein any trace amounts of the substance in liquid form which may be on the cassette will be absorbed by the stock.

5. A cassette assembly according to claim 3 wherein the flap extends inwardly of the sleeve from the first fold line to a terminal edge and wherein the terminal edge abuts a first lip on the cassette when the retaining member is in the first position.

6. A cassette assembly according to claim 5 wherein the sleeve first end adjoins the sleeve first side at the first fold line, the cassette first end and the cassette first side are positioned adjacent the sleeve first end and first side respectively, and wherein the lip is located on the cassette first side, the flap extends between the cassette first side and the sleeve first side, the first lip is positioned on the cassette first side.

7. A cassette assembly according to claim 6 wherein the second position comprises the flap being rotated about the hinge toward the first side of the sleeve and away from engagement with the first lip on the cassette.

8. A cassette assembly according to claim 1 further comprising a retarding means between the cassette and the sleeve for resisting travel of the cassette out of the sleeve through the sleeve first end.

9. A cassette assembly according to claim 8 wherein the retarding means comprises a projection which projects inwardly of the sleeve to engage a detent on the cassette.

10. A cassette assembly according to claim 9 wherein the forward direction is defined as the direction the cassette travels out of the sleeve through the sleeve first end, the backward direction is opposite of the forward direction and wherein the sleeve is formed of foldable stock and the projection comprises a tab formed of the stock and extending backwards from a second fold line to an edge, and wherein it is the edge of the tab that engages the detent.

11. A cassette assembly according to claim 10 wherein the stock is cardboard.

12. A cassette assembly according to claim 10 wherein the tab is moveable from a backward extending position where the tab edge engages the detent on the cassette and a forward facing position wherein the tab edge is out of engagement with the detent.

13. A cassette assembly according to claim 12 wherein a length dimension of the tab defined between the second fold line and the tab edge is small enough that the tab may rotate forwardly from the backward extending position to the forward facing position upon the application of a forward directed force on the cassette relative to the sleeve of a magnitude above a predetermined level.

14. A cassette assembly according to claim 12 wherein the tab is sufficiently flexible to buckle upon the application of a forward directed force on the cassette relative to the sleeve of a magnitude above a predetermined level and thereby move to the forwardly facing position.

15. A cassette assembly according to claim 12 wherein the magnitude of the predetermined force exceeds one half pound.

16. A cassette assembly according to claim 13 wherein the sleeve is formed of: an inner corrugated cardboard layer, the tab being formed of the inner layer; and an outer cardboard layer, the flap being formed of the outer layer.

17. A cassette assembly according to claim 1 further comprising at least one opening in the sleeve first side whereby a drive wheel may contact the cassette while the cassette is disposed within the sleeve for driving the cassette out of the sleeve through the sleeve first end.

18. A cassette assembly according to claim 1 wherein the substance is a hazardous fluid.

19. In a sterilizing apparatus comprising a chamber, a source of fluid sterilant, said sterilant being contained within at least one cell of a cassette, and a fluid delivery means for delivering the sterilizing fluid from the cell to the chamber, the improvement comprising a cassette delivery mechanism for delivering the cassette housing to the fluid delivery system, the cassette delivery system comprising:

a cassette assembly comprising:
the cassette having a first side and a first end;
a protective sleeve containing the cassette, the sleeve comprising a first side and a first end; and
a retaining member connected to the sleeve by a hinge at the sleeve first end, the retaining member being rotatable about the hinge from a first position in which the retaining member blocks the travel of the cassette out of the sleeve through the sleeve first end; and a second position in which the retaining member does not block travel of the cassette out of the sleeve through the sleeve first end; and
a receiving port for receiving the cassette assembly;
an opening member positioned to engage the retaining member when the cassette assembly is received within the receiving port and hold the retaining member in the second position; and
travel means between the receiving port and the fluid delivery mechanism for moving the cassette out of the sleeve through its first end and into the fluid delivery mechanism.

20. A sterilizing apparatus according to claim 19 wherein the sleeve is formed of foldable stock, the retaining member comprises a flap, the hinge comprises a first fold line in the stock and further comprising a biasing means which comprises the tendency for the stock to unfold along the first fold line.

21. A sterilizing apparatus according to claim 20 further comprising a retarding means between the cassette and the sleeve for resisting travel of the cassette out of the sleeve through the sleeve first end.

22. A sterilizing apparatus assembly according to claim 21 further comprising at least one opening in the sleeve first side whereby a drive wheel may contact the cassette while the cassette is disposed within the sleeve for driving the cassette out of the sleeve through the sleeve first end.

23. A sterilizing apparatus according to claim 19 further comprising a stop at the receiving port against which the sleeve abuts when received within the receiving port for limiting further travel of the sleeve into the receiving port.

24. A sterilizing apparatus according to claim 23 and further comprising a retainer which abuts an edge on the sleeve when the sleeve is received within the receiving port to inhibit travel of the sleeve out of the receiving port.

25. A method for delivering a cassette to a device comprising the steps of:
placing the cassette within a protective sleeve having a first end;
folding a flap on the sleeve inwardly of the sleeve first end to abut a retaining surface on the cassette and block travel of the cassette outwardly of the sleeve through the sleeve first end;
inserting an opening member into the cassette first end to abut the flap and move the flap out of engagement with the retaining surface;
sliding the cassette out of the sleeve through the sleeve first end and into a device.

26. A method according to claim 25 wherein the step of sliding the cassette out of the sleeve comprises the step of driving the cassette out of the sleeve with a machine.

27. A method according to claim 26 wherein the machine comprises at least one drive wheel which operates against the cassette through an aperture through the sleeve and the step of sliding the cassette out of the sleeve comprises driving the at least one drive wheel against the cassette thereby driving the cassette out of the sleeve through the sleeve first end.

28. A method according to claim 27 wherein the machine comprises one drive wheel which operates against the cassette through the aperture through the sleeve.

29. A method according to claim 27 and further comprising the step of driving the opening member against the retaining flap by driving the at least one drive wheel against the cassette assembly to drive the cassette assembly into contact with the opening member.

30. A method according to claim 29 and further comprising the step of resisting the travel of the cassette relative to the sleeve during the step of driving the cassette assembly toward the opener whereby to ensure that the at least one drive wheel drives the cassette assembly and not merely the cassette during this step.

31. A method according to claim 30 wherein the step of resisting the movement of the cassette relative to the sleeve comprises providing a protrusion on the sleeve which abuts the cassette.

32. A method according to claim 26 and further comprises the step of controlling the machine with an automatic controller.

33. A method according to claim 32 and further comprising the step of pushing the opening member against the retaining flap with the machine under the control of the automatic controller.

34. A method according to claim 25 wherein the step of pushing the opening member against the retaining flap comprises the step of driving the cassette assembly against the opening member with a machine.

35. A method according to claim 34 and further comprising the step of sensing the presence of the cassette assembly in position to be driven by the machine against the opening member and sending a signal thereby to the automatic controller.

36. A method according to claim 35 and further comprising the step of automatically reinserting the cassette into the sleeve with the machine.

* * * * *